United States Patent [19]

Keyes et al.

[11] Patent Number: 4,559,557
[45] Date of Patent: Dec. 17, 1985

[54] REGION-OF-INTEREST DIGITAL SUBTRACTION ANGIOGRAPHY

[75] Inventors: Gary S. Keyes, Hartland; Barry F. Belanger, Milwaukee; Anne L. Hall, Waukesha, all of Wis.

[73] Assignee: General Electric Company, Schenectady, N.Y.

[21] Appl. No.: 616,206

[22] Filed: Jun. 1, 1984

[51] Int. Cl.$^4$ .......................... G06F 15/42; H04N 5/32
[52] U.S. Cl. ...................................... 358/111; 378/99; 364/414; 364/415; 358/166
[58] Field of Search ................... 378/99; 364/414, 515; 358/111, 166

[56] References Cited

U.S. PATENT DOCUMENTS

| | | | |
|---|---|---|---|
| 3,706,851 | 12/1972 | Froehlich et al. | 358/183 |
| 4,245,244 | 1/1981 | Lijewski et al. | 378/99 |
| 4,335,427 | 6/1982 | Hunt et al. | 378/99 |
| 4,361,901 | 11/1982 | Daniels et al. | 378/106 |
| 4,367,490 | 1/1983 | Riederer | 358/111 |
| 4,445,226 | 4/1984 | Brody | 378/99 |
| 4,449,195 | 5/1984 | Andrews et al. | 358/111 |
| 4,454,507 | 7/1984 | Srinvasan et al. | 340/740 |
| 4,482,918 | 11/1984 | Keyes et al. | 378/99 |

Primary Examiner—Craig E. Church
Assistant Examiner—Charles F. Wieland
Attorney, Agent, or Firm—Fuller, House & Hohenfeldt

[57] ABSTRACT

In digital subtraction angiography a low X-ray energy temporal subtraction image is displayed on a video monitor. Regions in the temporal image frame that contain motion artifacts are outlined by using a cursor. The coordinates of the pixels in the defined outlined region are stored in a processor memory. The data for a related hybrid subtraction image are developed and stored. The processor then effects substitution of the hybrid subtraction image pixels, that fall within the same defined region, into the temporal subtraction image. The combined image data are transferred to a display controller memory which controls display of the combined image on a monitor. A method and means are provided for automatically determining the optimum value of the weighting coefficient applied to the high energy temporal subtraction image that results in the most complete cancellation of everything in the two images except the contrast medium filled blood vessel when the high and low energy temporal images are subtracted. A method and means are provided for altering the gain and offset of the hybrid image data in such manner as to match the hybrid image contrast and brightness with that of the temporal subtraction image.

8 Claims, 6 Drawing Figures

REGION-OF-INTEREST DIGITAL SUBTRACTION ANGIOGRAPHY

BACKGROUND OF THE INVENTION

This invention pertains to X-ray image subtraction method and apparatus for performing such methods, more commonly called digital subtraction angiography (DSA).

Digital subtraction angiography is an X-ray procedure for visualizing blood vessels in the body. The procedure involves making an X-ray image, called a mask image, of an anatomical region containing blood vessels of interest. The mask image is digitized and the digital data representative of the picture elements (pixels) in the mask image are placed in a digital frame memory. At some time, usually just before the mask image is obtained, an X-ray contrast medium, such as an iodinated compound, is injected into the blood circulation system. When the contrast medium reaches the blood vessels in the region of interest, a series of X-ray images are made and they are converted to digital data. The mask or precontrast image data are then subtracted from the postcontrast image data to cancel or subtract out all soft tissue and bone structure common to both images in which case data representative of the contrast medium filled blood vessel remains. The method just outlined is commonly called temporal subtraction imaging because of the substantial time lapse between acquisition of the pre-contrast image or a series of them and the postcontrast image or a series of them.

One of the problems associated with temporal subtraction techniques is that there may be a substantial loss of registration between the pre-contrast mask and post-contrast images due, primarily, to movement of soft tissue. Movement of soft tissue or anything else during acquisition of the pre-contrast and post-contrast images will result in artifacts appearing in the display of the subtracted or difference image data and these artifacts obliterate the desired image of the blood vessel whose interior walls are defined by the contrast medium.

With temporal subtraction it is often possible to achieve good cancellation or subtraction of bone, which usually does not move involuntarily, but some artifacts or misregistrations of pixels between the two images may result from involuntary tissue motion such as that due to swallowing, breathing, peristalsis and blood vessel expansion and contraction.

Another image subtraction technique is commonly called energy subtraction. Energy subtraction is based on the fact that X-ray attenuation by a body or any material is an X-ray energy dependent phenomenon and that the energy dependence is different for materials having different atomic number averages. In energy subtraction, an X-ray image of an anatomical region containing a blood vessel is obtained with a nominally low kilovoltage (kV) applied to the X-ray tube so the beam projected through the body has an energy spectral distribution within a band having low average energy. After the relatively low energy image is obtained, another image is obtained with a comparatively higher kV applied to the X-ray tube so the spectral band has a higher average energy. The two images in a pair can also be made in the opposite order, that is, the high energy exposure can precede the low energy exposure. For the sake of consistency and convenience, it will be assumed herein that the low energy exposure is the first one in a pair. The low and high energy images are acquired in a very short time interval, typically within 33 milliseconds, compared to a comparatively long time interval, typically 10 seconds between pre-contrast and post-contrast in temporal subtraction. Thus, the possibility of artifacts caused by patient motion is greatly reduced with energy subtraction. For ordinary tissue studies the two images may be made in the absence of any contrast medium. For angiographic studies, the two images are obtained when there is an X-ray contrast medium such as an iodinated compound present in the blood vessels. In any case, the high average energy image pixel data are subtracted from the low average image data and data representative of the difference between the two images remains. Prior to subtraction, the data are variously weighted or scaled to bring about cancellation of soft tissue by subtraction. The data could be weighted to bring about cancellation of bone also. However, it is not possible to cancel boney structures without also subtracting out most of the iodinated contrast medium which is really what one is depending on to define and allow visualization of the blood vessel.

A method called hybrid subtraction uses a combination of energy and temporal subtraction techniques. In hybrid subtraction, X-ray images are obtained at two different average X-ray energies, that is, with two different kilovoltages applied to the X-ray tube and the images are combined in a manner to suppress signals due to soft tissue. Methods for obtaining X-ray beams having low and high average energies for energy spectral bands are well known. One way is to apply a constant kilovoltage (kV) to the X-ray tube anode and interpose two different filters alternatingly in the beam. One filter is for softening the X-ray beam, that is, for removing high energy spectra above a low average energy band. One filter should have relatively low attenuation for X-ray photons having energies below the k-edge and high attenuation for energies above the k-edge to thereby remove high energy spectra. The other filter hardens the high energy beam and is composed of a material that attenuates or absorbs the low energy spectra intensely.

Low and high average energy X-ray beams can also be obtained by applying low kV and alternately, high kV to the X-ray tube anode. A preferred way for generating low and high energy X-ray beams is to switch the X-ray tube applied voltage and filters correspondingly.

In hybrid subtraction, a mask is obtained first by projecting a low average energy X-ray beam (hereafter called low energy beam or low energy spectral band) through the body followed by a higher average energy X-ray beam (hereafter called high energy beam or high energy spectral band) when X-ray contrast medium injected into the blood circulation system has not yet entered the blood vessels in the anatomical region being examined. The signals corresponding to the pixel intensities composing the image which consist primarily of bone and soft tissue acquired at the two energies, are scaled or weighted using appropriate constants (k), and then the images are subtracted to produce a mask image in which signals due to soft tissue variations are suppressed and boney structures remain. The data for a pair of high and low energy X-ray images are next obtained when the injected iodinated compound constituting the contrast medium reaches the vessels in the examination region. The data for this pair of images are acted upon by the same constant weighting factors that were used with the first pair of images and one image in this pair is subtracted from the other such that the resulting postcontrast image contains data representative of bone plus vessels containing contrast medium. The final step in hybrid subtraction is equivalent to temporal subtraction and involves subtracting the dual energy post-contrast image from the dual energy pre-contrast mask image to thereby suppress or cancel the bone and isolate the contrast medium containing vessels. A major advantage of hybrid subtraction over temporal subtraction alone is the reduced sensitivity to soft tissue motion artifacts because the soft tissue is suppressed or cancelled in both dual energy images.

Hybrid subtraction is a good technique for eliminating anything that may have moved during the time between obtaining the mask image and the postcontrast image or images. However, if there is no movement during ordinary temporal subtraction, wherein the postcontrast low or high energy images are simply subtracted from the pre-contrast mask image, then temporal subtraction images can be used because they generally have a better signal-to-noise ratio (SNR) than hybrid subtraction images. A higher SNR results in displayed images that have better contrast at a given noise level.

It is known that in some examination procedures there is a high probability that there will be soft tissue motion. Examination of the contralateral bifurcation of the carotid artery is one example. As many as fifty percent of the standard DSA carotid examinations result in images having soft tissue motion artifacts due to patient swallowing or an involuntary reaction to the presence of iodinated contrast medium. While hybrid subtraction is successful in eliminating these artifacts, the resulting image has an inherently lower SNR than temporal subtraction. Attempts have been made to improve SNR such as by image integration and noise reduction techniques, with varying degrees of success. Since noise in the hybrid subtracted image makes diagnosis for X-ray image interpretation more difficult, heretofore it has been the practice to provide for displaying a temporally subtracted image and the hybrid subtracted image separately and simultaneously. A temporal subtracted image provides the best overall image quality except where motion artifacts are present. A hybrid subtracted image has the motion artifacts eliminated but this image has more noise or a different noise texture than the temporal subtracted image. By providing both hybrid and temporal images on separate films or on separate video monitor screens, the interpreting radiologist could refer to both images and make a judgment as to the condition of a blood vessel that might be obscured wholly by motion artifacts in the temporal subtraction image and diminished by noise or low SNR in the hybrid image.

A second problem with hybrid DSA results from having the technician make a judgment as to a proper weighting coefficient or constant, k, to bring about elimination of motion artifacts when the images are subtracted. This is done empirically while viewing the result on a video monitor and often adds significantly to the total examination time. Moreover, an unskilled technician could fail to select the optimal weighting factors and thus not realize the full benefit of the hybrid subtraction technique.

SUMMARY OF THE INVENTION

An objective of the invention is to provide a method and apparatus for generating and displaying a temporal subtraction image such that, if significant motion artifacts are present in said image, at least the areas containing the artifacts in the region-of-interest can be subjected to hybrid imaging procedures and after some corrective processing is carried out, these areas can be patched into the temporal difference image with the result that the whole image has the diagnostic information substantially equivalent to a temporal image minus the artifacts.

Another objective of a preferred embodiment of the invention is to provide for automatic determination of the coefficients or constants, k, by which the low and high energy difference images data must be multiplied to obtain optimal subtracting out or cancellation of motion artifacts.

In accordance with the new method, low and high energy temporal difference images are acquired and the digital data representative of these images are stored on magnetic disk, for example. The image acquisition procedure is described in detail in Keyes, et al. patent application Ser. No. 371,683, filed Apr. 26, 1982, now U.S. Pat. No. 4,482,918. This patent is assigned to the assignee of the present application and is incorporated herein by reference.

Image acquisition involves exposing an anatomical region containing the blood vessel of interest to a sequence of closely successive pairs of high and low average energy X-ray beams. The sequence begins when the contrast medium that has been injected in the blood circulation system has not yet reached the vessel of interest. The low and high energy exposure pairs are obtained continuously right through the time when the contrast medium arrives in and departs from the vessel of interest. The latter is called the post-contrast interval. The low energy precontrast images are usually then summed and so are the low energy post-contrast images. The summed images are then weighted and one is subtracted from the other to yield data representative of a single low energy temporal difference image which is the best image if no motion artifacts are present. The high energy pre-contrast and post-contrast images can also be summed, weighted and subtracted to yield a high energy temporal difference image although it does not ordinarily have the contrast of the low energy temporal difference image.

Any good low energy pre-contrast image could be combined with any good post-contrast low energy image to produce a low energy temporal difference image but the summation or integrating process described in the preceding paragraph produces the best image ordinarily.

Since the data for each low and high energy pre-contrast and post-contrast exposure can be retrieved from storage at any time, the data is available to develop hybrid subtraction images at any time. Hybrid images, as previously mentioned, result from multiplying low and high energy temporal difference images by suitable weighting constants or coefficients, k, so that when the weighted images are subtracted, that is, combined, bone and soft tissue will cancel out and the iodine compound containing vessel will remain for visualization. However, the hybrid image will contain substantial noise ordinarily.

In accordance with the invention, the best temporal difference image is displayed on a video monitor and the digital pixel data representing this image are stored in the memory of a display controller. Assuming that motion artifacts are present for one polarity of the video signal, the artifacts will be manifested by black or nearly black irregularly defined areas and by adjacent bright areas in the image that will obscure and blank out the true configuration of the tissue or iodine contrast medium that is present and should be visible in the area. If the video signal has the opposite polarity, the artifacts will appear white. A video signal polarity that causes motion artifacts to appear black is assumed herein. Sometimes most of the image is clear and diagnosable although islands of motion artifacts exist in it. The new method makes it possible to produce a hybrid image of a predetermined area for it to be substituted or patched into the temporal difference image in areas where bothersome motion artifacts exist.

From the user's point of view, the invention involves defining four regions in the displayed temporal difference image that contains the motion artifacts. These regions are outlined by a cursor controlled by a trackball for instance. The first region is one or more that contains artifacts caused by patient motion. Any selected first region is designated $R_a$ where the subscript "a" indicates artifact.

A second region, designated $R_s$, contains predominantly good iodine contrast medium signal where "s" indicates signal. The second region can be chosen within the boundaries of the vessel where nothing but iodine compound, appearing white, is present.

A third region is one where hybrid subtraction is to be performed to bring out the vessel details that were obscured by motion artifacts. The third region is designated $R_h$ where "h" indicates hybrid. More than one of the so called third regions in the temporal subtraction image may be designated for hybrid image replacement.

The fourth region is used to measure offset, otherwise called background, $R_b$, where "b" indicates background. Background or offset is present everywhere in an image but it is discernible in areas that are relatively light or gray and lie outside of the high contrast areas. A constant amount of offset is purposely added to each digital pixel value after image acquisition. This is done to avoid production of negative numbers when corresponding pixels in low and high energy images are subtracted from each other. For instance, the image gray scale may range from zero to 255. Introducing an offset of about 100, for example, brings the lightest or lowest intensity range and this assures that the results of subtractions will always be positive. Negative pixel values would be meaningless in an image. Calculating time can be reduced if the computer is only required to handle positive numbers.

The data encompassed in the four regions $R_a$, $R_s$, $R_b$ and $R_h$ are used by the computer processor to develop data representative of a hybrid image that will be substituted or patched into the temporal difference image in place of the artifact containing areas to thereby permit visualization of the blood vessels that are actually in the area $R_h$. In accordance with the invention, the computer is programmed to calculate the weighting factor "k" that results in optimal cancellation of any anatomy that experienced motion during image acquisition. It also calculates an offset O* that is added to each pixel in the newly generated hybrid image regions and a gain, G, by which each pixel is multiplied, so the intensity of the pixels in the hybrid image will be on the same scale as the intensities in the temporal image, that is, the contrast in both images will be the same and the background or offset will also be the same.

A more detailed description will now be set forth in reference to the drawings.

DESCRIPTION OF A PREFERRED EMBODIMENT

Assume now that a sequence of alternate low energy and high energy pre-contrast and post-contrast X-ray exposures have been made as outlined above and that the digital pixel data representative of each of the resulting image frames is in storage. Assume further that the low energy pre-contrast mask image (comprised of one or the sum of several such images) is subtracted correspondingly from one or the sum, respectively, of post-contrast images to thereby yield the digital data representative of a temporally subtracted image. The temporal image data are stored in the memory of a video display controller which effects display of the image on the screen of the cathode ray tube of a video monitor. Now assume that the displayed temporal image is generally of good diagnostic quality but it contains areas exhibiting no detail such as black regions constituting motion artifacts and that the artifacts obscure the blood vessel in a critical area. In such case replacement of only the areas containing the artifacts with a hybrid image is indicated and can be achieved using the method constituting the present invention.

The high energy temporal subtraction image is also produced and stored in a frame memory for subsequent production of a hybrid subtraction image. The high energy temporal subtraction image need not be displayed but it could be if desired. For the sake of brevity it will be assumed that the high energy temporal subtraction image is no better than the low energy temporal subtraction image so the high energy image will not be processed for hybrid image replacement in any region-of-interest.

The method is based on the premise that any low or high energy temporal difference image is composed of three components. Thus, the following equations (Eqs.) can be written:

$$I_l = I_{s,l} + I_{a,l} + O_l \qquad (Eq. 1)$$

$$I_h = I_{s,h} + I_{a,h} + O_h \qquad (Eq. 2)$$

where $I_l$ represents the low energy (low kV) and $I_h$ represents the high energy (high kV) temporal difference image total signal.

$I_{s,l}$ ($I_{s,h}$) represent the signal components in the low and high kV, respectively, temporal difference images. This is the useful signal component since it represents the X-ray contrast medium that delineates the blood vessel.

$I_{a,l}$ ($I_{a,h}$) represent the signal components in the low and high kV, respectively, temporal difference images due to artifacts.

$O_l$ ($O_h$) represent the background or offset signal component added to the low and high kV images data, respectively, to assure that positive pixel values will result after image subtraction.

Recapitulating, "l" stands for low, "h" for high, "a" for artifact, "s" for useful signal and "O" for offset.

An expression for the hybrid image, "H", is as follows:

$$H = I_l - kI_h \quad \text{(Eq. 3)}$$

where "k" is the weighting factor or hybrid combination coefficient by which the high kV image, $I_h$, pixel data must be multiplied for cancelling artifacts caused by tissue motion and letting remain signal due to contrast medium when the temporal difference images are subtracted.

Rewriting Eq. 3 in terms of Eqs. 1 and 2 yields the following:

$$H = I_{s,l} - kI_{s,h} + [I_{a,l} - kI_{a,h}] + O_l - kO_h \quad \text{(Eq. 4)}$$

Since it is the artifacts, a, signal that one desires to subtract out or cancel, the terms in parentheses in Eq. 4 can be set equal to zero in which case the optimal value of "k" can be determined from the measured values of the artifact signal in the low and high kV temporal difference images. Thus, $$k = \frac{I_{a,l}}{I_{a,h}} \quad \text{(Eq. 5)}$$

How the contribution of the artifact signal can be measured will be described later.

Now, in place of the hybrid image described in Eq. 3, a new hybrid image, H*, is defined as follows:

$$H^* = GH + O^* \quad \text{(Eq. 6)}$$
$$= G(I_l - kI_h) + O^* \quad \text{(Eq. 6a)}$$

where:

G = a gain factor by which the basic hybrid image, H, pixel data or image frame must be multiplied to maintain the contrast due to the iodine producing signal in the hybrid image, H*, at the same value as contrast in the temporal difference image which is to have the motion artifacts removed by patching in H*.

O* = an offset factor that maintains the offset in the new hybrid image at the same value as in the low temporal difference image being subjected to artifact removal.

H in Eq. 6 is composed of the first, second, fifth and sixth terms in Eq. 4. The terms in parentheses in Eq. 4 are left out because in producing a basic hybrid image, H, the artifacts are cancelled out by the choice of k given by Eq. 5.

The following results from substituting the value of k given in Eq. 5 into Eq. 4 and comparing to Eq. 1:

$$G = \left(1 - \frac{I_{a,l}}{I_{a,h}} \cdot \frac{I_{s,h}}{I_{s,l}}\right)^{-1} \quad \text{(Eq. 7)}$$

and $$O^* = O_l \left[1 - G\left(1 - k\frac{O_h}{O_l}\right)\right] \quad \text{(Eq. 8)}$$

The images are acquired through a video camera that views the optical image version of the X-ray image which appears on the output phosphor of an X-ray image intensifier. The offset can be added to the analog video signals which are output from the camera. However, even though the same offset value is added to the signal, the actual offsets in the resulting low and high kV images after they are converted to digitized pixels may differ. One reason is that the video camera and its electronic chain may respond non-linearly to the different brightness levels in the images. Another is that the analog-to-digital converter responds differently to signals at different levels or to images acquired at different times. As will be shown later, in accordance with the invention, the actual offsets $O_l$ and $O_h$ in the low and high temporal difference images can be determined for use in forming the hybrid image H* that will be patched into the displayed low kV temporal difference image.

A method will now be described for determining the parameters k, G and O* which are needed in Eqs. 6 or 6a to produce a new hybrid image which, when inserted in a selected region in the temporal difference image that contains motion artifacts, will match the surrounding temporal difference image in pixel intensity scale or brightness and in relative contrast, will restore the image information obliterated by the artifacts to diagnostic quality and will be free of motion artifacts.

Figure 2:
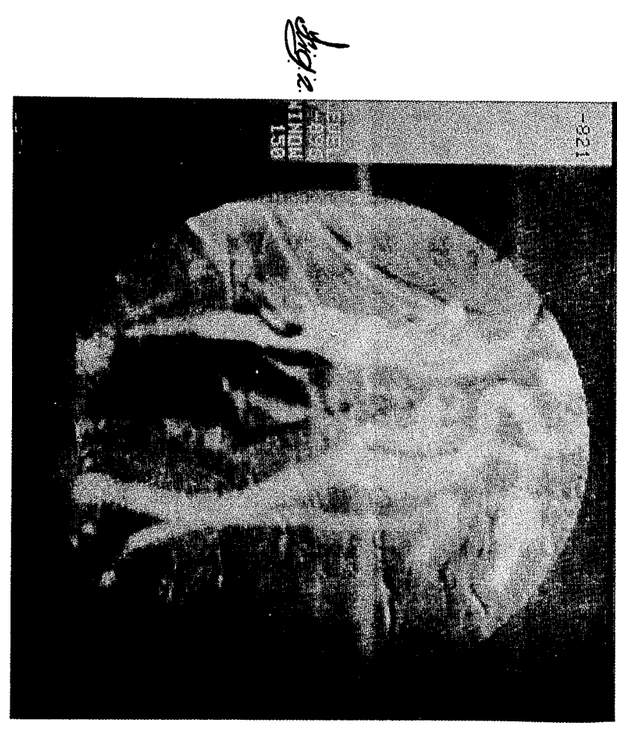
FIG. 2 is a temporal subtraction image showing a motion artifact, which is the irregularly shaped region in the lower left quadrant of circular image that appears nearly black and wherein the lightest regions are the contrast medium filled blood vessels, particularly the carotid arteries.

Assume, that by using the X-ray imaging apparatus that is yet to be described, the data representative of the best temporal difference image obtainable by subtracting a low energy pre-contrast or mask image from a low energy post-contrast image has been acquired. The pixel data for this image frame are in the memory of a video display controller and the image generated from these data is being displayed on the cathode ray tube screen of a video monitor as in FIG. 2. The blood vessel is considered to be filled with and delineated by X-ray contrast medium. In the example shown, a typical artifact due to tissue motion during image acquisition appears as a black island in the lower left quadrant of the circular temporal difference image in FIG. 2. It is, thus, impossible to determine what the blood vessel looks like in the area obliterated by motion artifact although details everywhere else in the image may be clear. Supplanting only the artifact area with a hybrid image is required.

As will be discussed more fully later, the apparatus comprises a computer and suitable memories for processing image data. It also includes a trackball which can be rotated by the user in any direction to develop and move a cursor on the monitor screen for pointing to or tracing around any regular or irregular region in the temporal image being displayed. For the time being accept the fact that the computer system has the capability of determining the coordinates of all pixels encompassed by a cursor trace that is written over the displayed temporal subtraction image.

Figure 3:
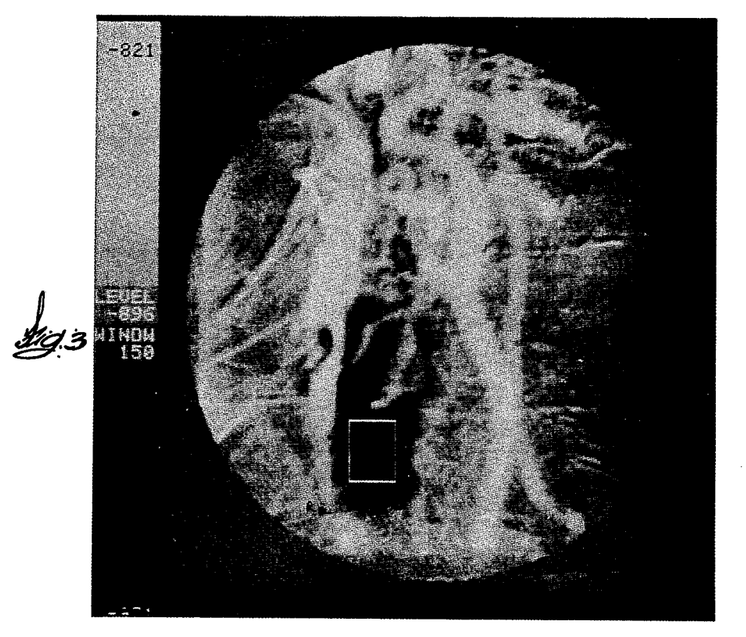
FIG. 3 is the same image wherein a region ($R_a$) representative of the motion artifact is delineated by a rectangle written with a cursor on the displayed image.

In accordance with the new artifact removal method, the operator is required to select or define four regions-of-interest in the displayed temporal subtraction image. The first region, $R_a$, is a sample of the region containing the larger artifact. This region is defined by the white outline rectangle in the lower left quadrant of the circular image area in FIG. 3. The defined region is written on the display screen by using a cursor writing trackball as will be elaborated later. The coordinates of the pixels in the defined region are held in computer memory. The defined region can have any shape required to encompass a region representative of a parameter such as $R_a$. The region might be circular, square or pear shaped for example.

Figure 5:
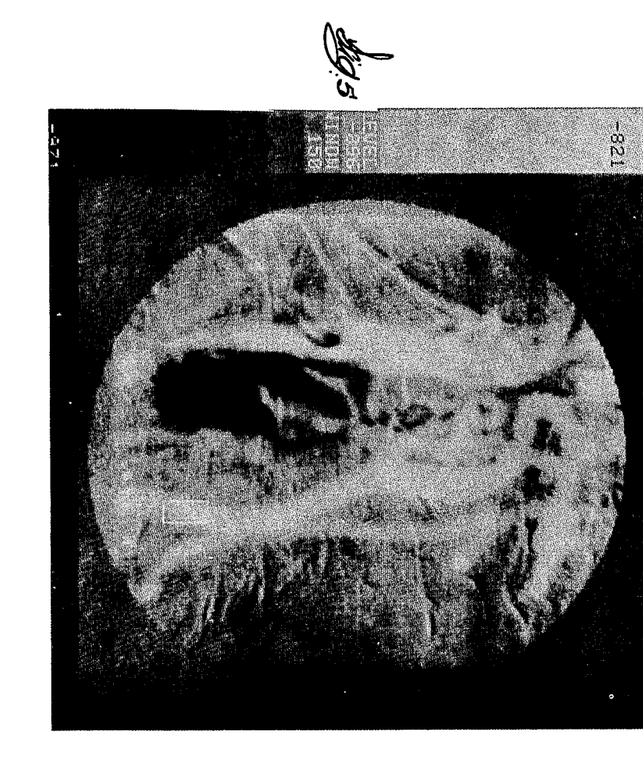
FIG. 5 is the same image wherein a region ($R_s$) representative of the good signal or image density in the contrast medium filled the blood vessel of interest.

A second region-of-interest, $R_s$, that must be selected and defined is one that exhibits the density of the X-ray opaque medium in the blood vessel. This region happens to be defined by the white outlined rectangle that appears in the lower right quadrant of the image in FIG. 5. The region is defined in what is obviously a contrast medium filled vessel because of its uniform density. An ellipse with its long axis vertical or a parallelogram shaped region might have been used in this case. In any case the coordinates of the pixels in the defined region, $R_s$, are determined and stored in computer memory. $R_s$ is the good signal that represents the blood vessel which is to be visualized with the greatest clarity.

Figure 4:
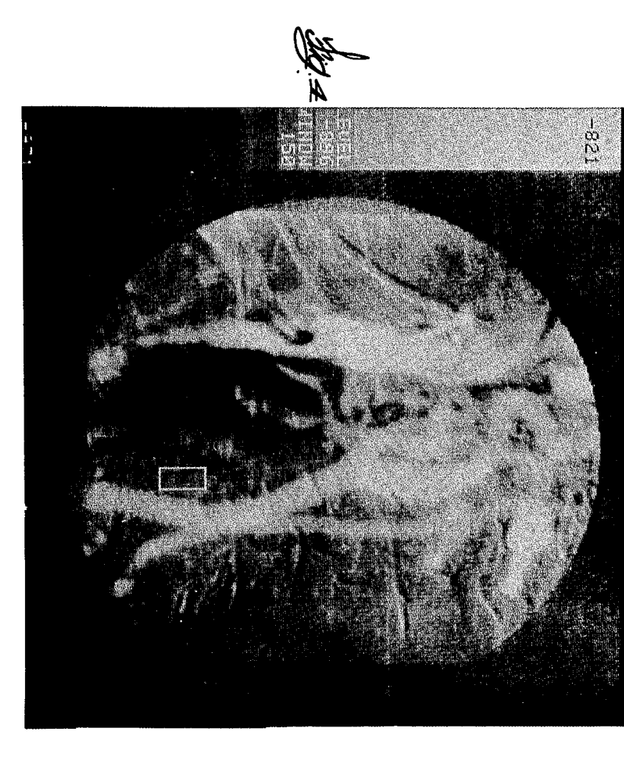
FIG. 4 is the same image wherein a region ($R_b$) representative of background or offset is delineated with the cursor.

A third region-of-interest is one that reveals the background or offset density, $R_b$, and is shown by the white rectangle in FIG. 4. Offset, $R_b$, can be picked out by a relatively inexperienced operator by looking for an area in the temporal subtraction image over which there is substantially no density change and that lacks any perceptible anatomical structure changes. Offset is essentially background and can be determined much as anyone would perceive background or large areas of uniformity in a painted scene. The coordinates of the pixels in the region-of-interest, $R_b$, are computed and stored in computer memory.

Figure 6:
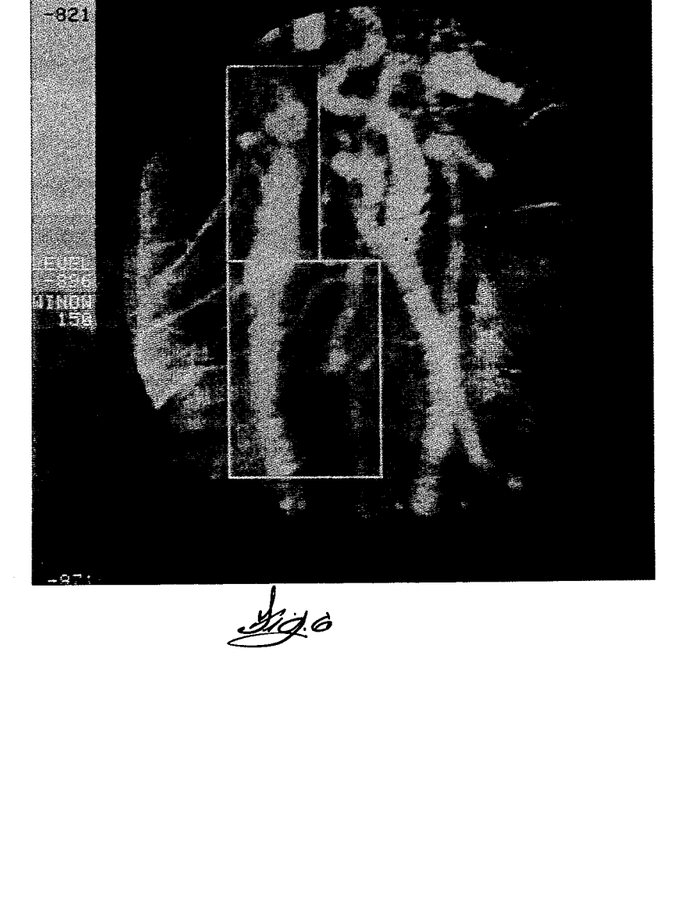
FIG. 6 is the same temporal subtraction image wherein two regions ($R_h$) delineated by white rectangles are the regions wherein a modified hybrid subtraction image supplants the temporal subtraction image.

A fourth region-of-interest, $R_h$, is one in which the hybrid subtraction image has been substituted for the corresponding region in the displayed temporal subtraction image. Two cursor defined rectangles outlined in white in FIG. 6 illustrates that the operator decided that two contiguous regions of different shapes could profit by having a modified hybrid subtraction image substituted. The regions, of course, do not have to be contiguous and more than two which might benefit by hybrid image replacement might be defined. In FIG. 6 example, the region, $R_h$, was defined by the operator to include the obvious artifact containing area plus areas where there could be uncertainty. The coordinates of the pixels in the $R_h$ regions were determined from the temporal subtraction image. Note that FIG. 6 is the finished product. The modified hybrid subtraction image has been inserted already by the method to be further explained. The motion artifacts, $R_a$, exhibited in the basic FIG. 2 temporal subtraction image are reduced. Blood vessel configurations formerly obscured by the artifacts are now visible for diagnosis. Of course, when the image is displayed for diagnosis the cursor could be turned off so as to not distract the diagnostician.

One should recognize that the four regions-of-interest can be selected in any order.

After the four regions-of-interest just described have been defined the following operations are carried out.

1. Within the cursor defined background region, $R_b$, form the sum of all the pixel intensity values separately for the low kV and high kV temporal difference images. Identical regions, $R_b$, are used in the low and high kV images. The sums define the offsets, $O_l$ and $O_h$, and are given by:

$$LO_l = \sum_{j=1}^{L} I_{b,l,j}$$

$$LO_h = \sum_{j=1}^{L} I_{b,h,j}$$

L simply implies that it is the total number of pixels in the define region $R_b$, that it determined. "I" represents image intensity only in the background region.

2. Within the cursor defined artifact exhibiting region, $R_a$, form the sum of all the pixel intensity values separately for the low kV and high kV temporal difference images. Identical regions, $R_a$, are used in the low and high kV images. These sums are given by:

$$A_l = \sum_{j=1}^{N} I_{a,l,j} - NO_l$$

$$A_h = \sum_{j=1}^{N} I_{a,h,j} - NO_h$$

N is the number of pixels in the defined region, $R_a$, which could be different, and usually is different, than the number of pixels, L, in the offset region-of-interest and the number of pixels, M, in the contrast medium signal region-of-interest. I is the image intensity in region $R_a$.

3. Compute the ratio of the sums in preceding operation 2 which yields the value of the optimal weighting coefficient "k", according to Eq. 5, for cancelling the motion artifact.

$$k = \frac{A_l}{A_h}$$

4. Within the defined region-of-interest, $R_s$, which represents valid signal due to X-ray contrast medium in the blood vessel, form the sum of all the pixel intensity values separately for the low kV and high kV temporal difference images. Identical regions, $R_s$, are used in the low and high kV images. Identical regions, $R_s$, are used in the low and high kV images. These sums are given by:

$$S_l = \sum_{j=1}^{M} I_{s,l,j} - MO_l$$

$$S_h = \sum_{j=1}^{M} I_{s,h,j} - MO_h$$

where M is the number of pixels in regions $R_s$.

5. Compute the ratio of the sums in preceding operation 4 and substitute in Eq. 7 to determine the hybrid image gain factor G, that will maintain the same contrast as in the temporal difference image:

$$G = \left(1 - \frac{A_l}{A_h} \cdot \frac{S_h}{S_l}\right)^{-1}$$

6. Substitute the values of k, G, $O_l$ and $O_h$ into Eq. 8 to thereby determine O*, the offset to be added to the hybrid image.

7. Now for each pixel within the selected region-of-interest, $R_h$, compute the intensity value to form the hybrid image H* that is to be inserted in the region or regions, $R_h$, defined in the temporal difference image using Eq. 6 and the values found for k, G and O*.

8. Now, in the low energy temporal difference image, replace the pixel values within the region, $R_h$, by the pixel values calculated in preceding operation 7 and display the resulting composite or patched image on a video monitor.

It will be seen that the procedure just described maintains the comparatively high signal-to-noise ratio that is usually present throughout most of the temporal difference image. Where there are motion artifacts, an optimal hybrid subtraction is performed to eliminate artifacts. There is no trial and error required by the operator to find the optimal weighting factor "k" for producing a hybrid image in which motion artifacts would cancel out. The inserted limited area modified hybrid image is conformed to the contrast and intensity levels of the temporal image so it is all but impossible to detect that a limited hybrid image has been patched in. The former need for having two images, a full temporal difference image and a full hybrid image or display next to each other is obviated. The difficulty of deriving true diagnostic information from the noisier unmodified traditional hybrid image is reduced. The only intervention by the operator, beyond acquiring the images, is to define the four regions-of-interest needed for the optimization procedure.

Figure 1:
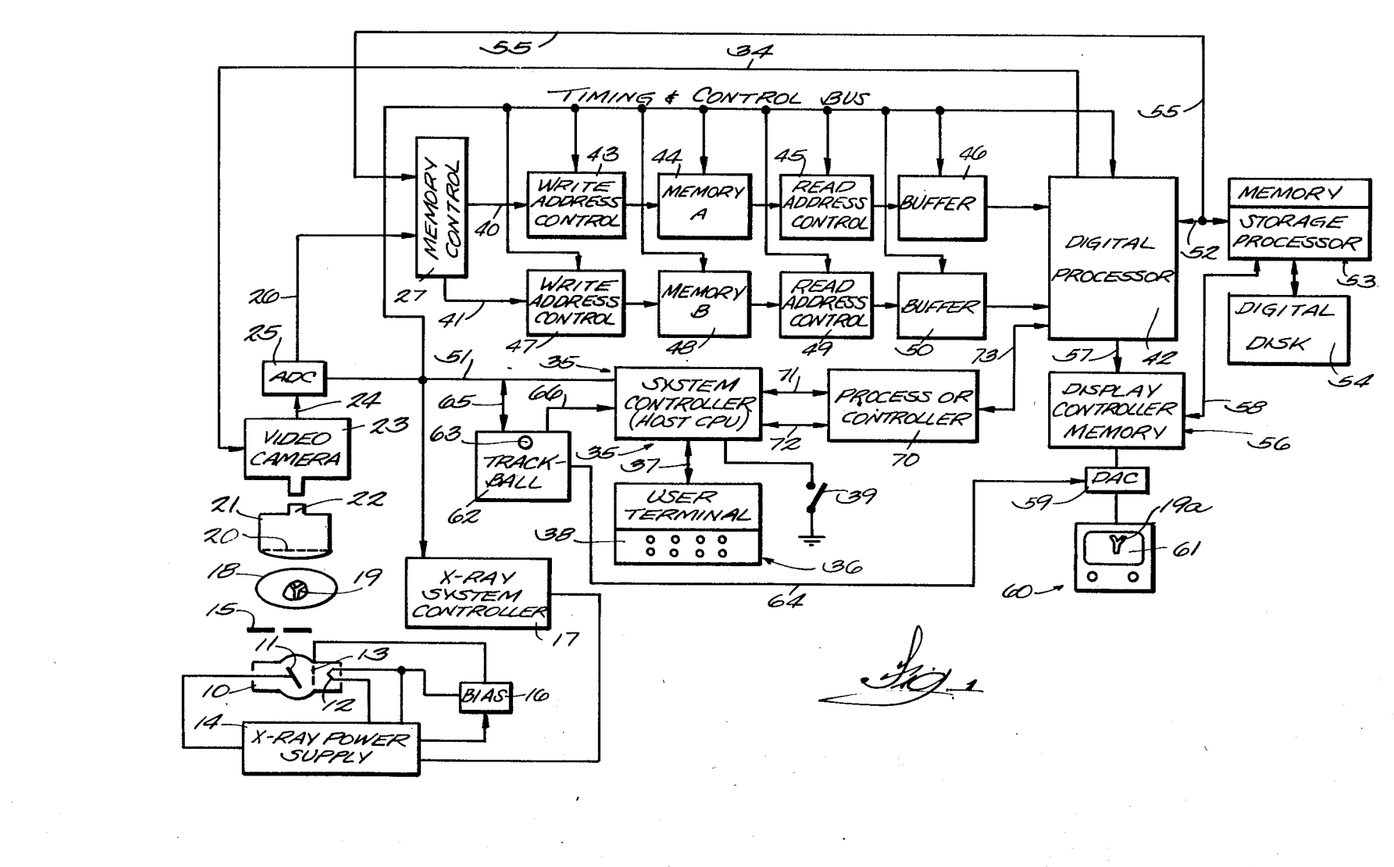
FIG. 1 is a block diagram of an X-ray system for performing the new hybrid image substitution method.

Now that the steps involved in the preferred method of replacing motion artifact containing regions in a concurrently displayed temporal difference image with a hybrid subtracted image have been described, the new hardware configuration for processing the image data will be examined in reference to FIG. 1.

The part of FIG. 1 involved in acquiring alternate closely successive high and low energy (high and low kV) is known. It comprises an X-ray tube 10 having an anode 11, a cathode 12 and a control grid 13. The X-ray power supply is designated by the block marked 14. The supply contains the customary high voltage step-up transformer, rectifier and switching circuits, none of which are shown. It is sufficient for present purposes to recognize that the power supply can apply low kilovoltage (kV), on the order of 70 kV for example, between the anode 11 and cathode 12 alternatingly with applying high kV, on the order of 130 kV, in quick succession to cause emission of X-ray beams having low average photon energy and high average photon energy, respectively. Movable X-ray filters 15 can be inserted in the beam synchronously with the low and high kV beams. Suitable filters for narrowing the X-ray photon energy spectrum of the low and high kV beams are well known in the art.

A bias voltage supply is symbolized by block 16. When the low kV is being applied to the X-ray tube anode, the bias supply is controlled to apply zero bias voltage to the control grid 13 in which case the X-ray tube current will be higher compared to the current when the high kV is applied to the anode and a negative bias voltage is applied to the grid. The timing and synchronization of the low and high energy X-ray pulses is accomplished with a known X-ray system controller which governs power supply 14. A suitable X-ray power supply for generating high and low energy beams is described in Daniels, et al. U.S. Pat. No. 4,361,901 which is assigned to the assignee of this application.

A sequence of pairs of low and high energy X-ray beams are projected through a body, represented by ellipse 18, which exhibits a bifurcated blood vessel, 19 for example, whose condition is to be determined by way of the digital subtraction angiography procedure. The X-ray images, containing the soft tissue, bone and vessel in the anatomical region through which the X-ray beams project, fall on the input phosphor 20 of an image intensifier 21. Corresponding optical images appear on the output phosphor 22 of the intensifier. A video camera 23 views the optical images and converts them to analog video signals which are output on line 24. The analog signals are converted to digital signals with an analog-to-digital converter (ADC) 25. The digital signal values correspond to the intensities of the picture elements (pixels) of which each image frame is composed. The digital values are typically 12-bits deep. They are inputted by way of a bus 26 to a system component called memory control which is represented by the block marked 27. The structure and functions thus far described in reference to FIG. 1 are generally known to those involved in digital fluorography technology.

The system in FIG. 1 is governed by a host central processing unit (CPU) which is called the system controller and is symbolized by the block marked 35. The CPU block 35 represents a complete computer processing system including the memories for program instructions and the operating system and the arithmetic logic circuits and so forth which are customarily parts of a host CPU. The operator interface with the system is represented by the block marked user terminal and the numeral 36. It is coupled to CPU 35 for bidirectional communication with the system by way of multiple digital signal lines 37. The operator selects X-ray image acquisition procedures and image data processing procedures by using the keyboard 38 that is associated with the terminal. A hand operated switch 39 is shown next to CPU 35. Assume that when this switch is closed momentarily it will inform the CPU to perform the initializing functions and operations for carrying out an X-ray exposure sequence. Such operations would include among others measuring the time from the closing of switch 39 to the start of the low and high energy pre-contrast exposure pairs are to start, and the time at which the X-ray opaque or contrast medium is to be injected, so as the sequence proceeds, the post-contrast images will be acquired too.

In FIG. 1 the raw low and high energy images data are fed through memory control 27 during original image acquisition and they output on multiple digital lines 40 and 41 to two similar image data channels both of which lead to a digital processor 42. The first channel includes write address control 43, memory A or 44, read address control 45 and a buffer 46. The second channel includes write address control 47, memory B or 48, read address control 49 and buffer 50. The components just listed, the memory control 27 and the digital processor 42 are all coupled to timing and control bus 51 which runs out of system control CPU 35 so all components in the system can be controlled by the CPU to perform specified functions and to do so at the proper times during original image data acquisition and during image data reprocessing.

The data output lines or bus 52 from processor 42 are input to a block called storage processor which is marked 53. The storage processor 53 is basically a device for interfacing with a digital disk recorder marked 54. Processor 53 contains a digital memory, not shown, for holding the data representative of at least four image frames at one time. Image data can be outputted from processor 42 to bus 52 and then back to the memory control 27 by way of a feed back or wrap around bus 55. Image data can also be accessed from disk recorder 54 through storage processor 53 and fed by way of wraparound bus 55 to memory control 27. This would be done in connection with forming a region-of-interest hybrid subtraction image for substitution in the region in a motion artifact exhibiting temporal difference image, for example, as has been described earlier.

Assume now that original image acquisition is underway. The digital data for the low and high energy images may be fed right through from one of the output buses 40 or 41 directly to storage processor 53 and then to digital disk 54 for storage. In other words, the components in the channels are set up by the CPU control signals to simply pass acquired images. Hence, the raw data, that is, the data for each low and high energy exposure is stored on disk 54 so the data is always available for processing in any desired way without requiring further X-ray exposures.

Any low energy (low kV) or high energy (high kV) pre-contrast or post-contrast image obtained during an exposure sequence and any generated temporal difference or energy difference image can be displayed with the system at any time. To display an image frame, the digital pixel data that represents it is accessed from disk recorder 54 and stored in the full frame memory of a video display controller represented by the block marked 56. These digital data are transmitted by either bus 57 or 58.

As is well known, the video display controller can store the digital pixel data for an image frame and output the pixel signals essentially in a raster scan format. The digital signal values that are output from video display controller 56 are converted to analog video signals in a digital to analog converter (DAC) 59. The analog video signals drive a raster scanned video monitor 60 on whose cathode ray tube screen the image of the blood vessels 19a is displayed.

As indicated earlier, development of a hybrid subtraction image in a region-of-interest encompassing the motion artifact containing area of a temporal difference image that is on display requires delineating four regions with a cursor generated with a trackball control. The regions were selected to exhibit $R_a$, (primarily artifact); $R_b$, (background or offset region); $R_s$, (desired signal or pixel intensity due to X-ray contrast medium in the blood vessel); and $R_h$, (region in the temporal difference image to be replaced by the hybrid subtraction image). The trackball is symbolized by the block marked 62 in FIG. 1. Graphics or cursor generators are described in detail in Lijewski, et al. U.S. Pat. No. 4,245,244 and Srinivasan, et al. U.S. Pat. No. 4,454,507 which are owned by the assignee of this application. For present purposes it is sufficient to accept that the ball 63 of the trackball control can be rotated in all directions and that it will produce a series of pulses at corresponding x,y coordinates to define a bright cursor on video display screen 61 which delineates any desired enclosed regions such as $R_a$, $R_b$, $R_s$ and $R_h$ in FIG. 2. The trackball pulses are transmitted by way of line 64 and are injected into the video signal at DAC 59 to define the cursor which is written over the image being displayed on the screen. Temporal image data stored in the memory of video display controller 56 is not affected by the cursor signals. The trackball is coupled to timing and control bus 51 by way of bus 65. The cursor signal information is supplied to host CPU 35 by way of bus 66 which stores the location and coordinate data for the cursors that define the four regions.

Image data processing, manipulation of image data and arithmetic operations are carried out in digital video processor 42. A suitable DVP is described in the application of Andrews, et al., Ser. No. 321,307, filed Nov. 13, 1981, now U.S. Pat. No. 4,449,195 which is assigned to the assignee of this application and is incorporated herein by reference. This patent shows that the DVP is comprised of arithmetic logic units, multiplexers and memories interconnected by buses. There is a processor controller interposed between a host CPU and the DVP. The DVP provides the timing signals to the video camera 23 by way of line 34. This assures that certain operations will be carried out during vertical blanking without interrupting image data acquisition. The host CPU has the program governing image acquisition and image data processing. When a function such as image acquisition is to be performed the CPU sends a small number of appropriate digital instruction words called a recipe, to the processor controller. The processor translates the instructions into a series of command words which variously activate or deactivate selected components and data paths in the DVP so that the components will perform the desired operations on the image data such as summing or integrating low and high kV image pixels, multiplying image data by coefficients, converting raw pixel data to natural logarithm values, and combining or subtracting images. The patented DVP control method, however, lacked some features which, according to the present invention, are provided for. For instance, in the prior system when one digital memory was read out for the purpose of operating on its data and writing the result in another memory, all locations in the other memory were written into. In other words, being compelled to read and write out of and into all or none of the memory consumes substantial amounts of computer time. In accordance with the invention, a mode is described which permits reading out and writing pixels within selected parts of an image frame such as in the regions $R_a$, $R_b$, $R_s$ and $R_h$. Thus, for example, where the CPU must sum the pixels in a few of these regions or transfer part of a hybrid image to the display controller containing the temporal image data, only the pixels of interest need to be handled.

In FIG. 1, a block marked 70 represents the processor controller. It is coupled to CPU 35 by way of a control and timing bus 71 and a data bus 72. A bidirectional bus 73 couples processor controller 70 to the DVP 42. The host CPU, as indicated earlier, has stored the locations of the image pixels that are identified by the cursor fields. The full hybrid image is formed in response to the operator providing the command to form this image by using the user terminal 36. The hybrid image is formed, based on data accessed from digital disk 54, and stored in one of several full frame memories in DVP 42. The new or modified hybrid image H* is then formed by having the arithmetic logic units in the DVP execute Eq. 6a. The result is stored in a memory in the DVP. The CPU has previously calculated the gain G and O* which is sent to the arithmetic units in the DVP by way of processor controller 70. Now what remains to be done is substitute only that region, $R_h$, of the modified hybrid image which was defined by the cursor for replacing the corresponding region in the displayed temporal difference image.

The modified hybrid image is written into the selected region $R_h$ in the temporal image in minimum time because, in accordance with the invention, only the pixels within the defined boundaries of $R_h$ are extracted from the modified hybrid image which has been formed and stored in a DVP memory. To achieve high speed writing the special write address control and read address controls 43 and 45, for example, are provided. These controls permit writing into and reading from a digital memory in an unconventional way. Typically, random access memories (RAM) contain a register into which pixel data that is to be written into the memory array is stored temporarily. But when writing into the memory is enabled, data transfer time begins and does not end until all locations in the memory are sequenced. In other words, writing into and reading out of a memory is an all or none situation. Writing in all of a memory, even writing mostly zeros takes considerable time. In the present invention, reading and writing only those pixels within the region, $R_h$, of the modified hybrid image is desired.

In accordance with the invention the full low energy temporal subtraction image frame is loaded into memory A which is also marked 44. To obtain the temporal subtraction image, the raw pixel data are transferred from the digital disk 54 to the digital processor 42 wherein the individual digital pixel values are converted to natural logarithm values. The operator has the option of integrating or summing several or all of the low energy pre-contrast and the same number of post-contrast images data before one integrated data set is subtracted from the other to get the low energy temporal subtraction image or the operator can just choose one good precontrast and one good post-contrast image for subtraction. In any case, the low energy temporal subtraction image is loaded from digital processor 42 to memory A or 44 by way of wrap-around bus 55.

The full modified hybrid image H* is similarly formed in digital processor 42 with appropriate gain, G, and offset O* applied as previously described and this image is loaded into memory B or 48.

Now the region $R_h$ in the modified hybrid image, H*, that is to be substituted in the temporal subtraction image is read out of memory B, (using read address control 49) passed through digital video processor 42, wrap-around bus 55 and write address control 43, thereby overwriting the corresponding pixel values in memory A defined by $R_h$. Thus, the temporal image has the modified hybrid image region-of-interest inserted in it. The entire combined temporal and modified hybrid image data are then read out of memory A through digital video processor 42 and into the memory of display controller 56. The temporal image with a modified hybrid image replacing part of it, as in FIG. 6, is then displayed as image 19a on screen 61 of video monitor 60.

The image 19a is essentially the contrast medium filled blood vessel of interest. The motion artifact is eliminated but the parts of the vessel formerly obscured in the preferred temporal difference image by the artifact become visible and well defined so an accurate assessment of the blood vessel's condition can be made by the diagnostician.

The preferred method of replacing a hybrid image in motion artifact containing regions of a temporal image has just been described. In the preferred method the weighting coefficient is determined without operator involvement and time for developing the modified and exact replacement hybrid image is rapid. The new concept of inserting a modified hybrid image in temporal subtraction image regions that contain motion artifacts can be performed in other ways. The most basic approach is to simply display the temporal subtraction image and define the regions, $R_h$, using the cursor, which contain artifacts. The temporal subtraction image frame is stored in memory A and, of course, the display controller 56 memory. An ordinary hybrid subtraction image can be developed and stored in memory B. The pixel values in the region, $R_h$, in the temporal subtraction image in memory A, can then be replaced with the pixels in the corresponding region in the hybrid subtraction image as previously described. Then the temporal image with the unmodified hybrid region can be displayed. This approach improves diagnostic efficiency as a result of reducing the motion artifacts with the hybrid subtraction step although the hybrid image will not ordinarily have the same brightness level or offset nor the same contrast as the temporal image.

In the method described in the preceding paragraph, it is assumed that the system was provided with operator controlled means for selecting several different values of the weighting coefficient, k, so a value could finally be used which resulted in the best cancellation of everything while letting the contrast medium filled blood vessel remain. The best value of k for the particular procedure is stored. This basic method simply amounts to carrying out Eq. 3 to get, H, the hybrid image. The unique feature is the substitution of a hybrid subtraction image region into a temporal subtraction image.

The basic method just described is improved by adding another step which matches the contrast in the temporal and hybrid subtraction images. It is to provide means for permitting the operator to multiply the right side of Eq. 3 by a choice of several different gain factors, $C_g$, so Eq. 3 becomes:

$$H = (C_g)(I_l - kI_h) \qquad \text{(Eq. 3a)}$$

In Eq. 3a, of course, as in the case of Eq. 3, the raw image data are converted to their logarithmic equivalents before the low energy temporal subtraction and the high energy temporal subtraction images are formed.

The method described in the preceding paragraph can be still further improved by providing for matching the offsets or background level in the temporal and substituted hybrid subtraction image as well as matching the contrast. Here the system is provided with means that lets the operator try different offset values ($O_b$) that can be added to the pixels until one is found that results in the brightness levels of the temporal and contrast corrected hybrid replacement images matching. This is expressed as:

$$H = (C_g)(I_l - kI_h) + O_b$$

We claim:

1. A digital subtraction angiography method comprising the steps of:

forming a temporal subtraction image of an anatomical region and storing the digital signal values corresponding to the intensities of the picture elements (pixels) composing said image, converting said digital signal values to analog video signals for effecting display of the temporal subtraction image on a video monitor, forming a hybrid subtraction image and storing the digital signal values corresponding to the intensities of the pixels composing said hybrid subtraction image, defining in said temporal subtraction image a region or regions in which the values of the pixel signals are to be replaced by the values of the corresponding pixel signals in a corresponding region or regions, respectively, in said hybrid image, inserting the digital pixel signal values from said region or regions of said hybrid image in place of the corresponding pixel signal value in said stored temporal subtraction image, and converting the digital pixel signals representative of the resulting combined image to analog video signals for effecting display of the resulting image on the video monitor.

2. The method according to claim 1 wherein said temporal subtraction image is the low energy temporal subtraction image resulting from subtracting pixel signal values representative of one or an integration of more relatively low energy X-ray exposures made before an X-ray contrast medium that has been injected into the anatomy has reached a blood vessel of interest and a corresponding one or a similar number of integrated images, respectively, of said relatively low energy exposures made after said contrast medium has reached the vessel of interest.

3. The method according to any one of claims 1 or 2 including the step of multiplying the pixel signal values included in at least the corresponding defined region in said hybrid image by a gain factor, said factor being of such value as to produce substantially the same contrast in the hybrid subtraction image that is inserted as the pixels in the temporal subtraction image when the combined images are displayed.

4. The method according to any one of claims 1 or 2 including the step of adding a constant value to the pixel signal values included in at least the corresponding defined region in said hybrid image, said constant being of such value as to result in the pixels in the hybrid subtraction image that is inserted having substantially the same brightness as the pixels in the temporal subtraction image when the combined images are displayed.

5. The method according to claim 3 including the step of adding a constant value to the pixel signal values included in at least the corresponding defined region in said hybrid image, said constant being of such value as to result in the pixels in the hybrid subtraction image that is inserted having substantially the same brightness as the pixels in the temporal subtraction image when the combined images are displayed.

6. A digital subtraction angiography method such that regions in a temporal subtraction image containing artifacts are replaced by a modified hybrid subtraction image to enable visualization of a blood vessel that is obscured by an artifact, comprising the steps of:

forming the temporal subtraction image frame and storing the digital signal values corresponding to the intensities of the picture elements (pixels) composing the image in a first digital memory, converting said pixel signal values to analog video signals for effecting display of the temporal subtraction image on a video monitor, forming a hybrid subtraction image (H) at least including a region ($R_h$) in said temporal subtraction image which contains an artifact and is a region in said temporal image whose pixels will be replaced by the pixels of a modified hybrid image (H*), and storing the corresponding digital pixel signals representative of at least said region in the hybrid subtraction image in a second digital memory, producing a modified hybrid image, H*, by multiplying each of the pixel values in said region, $R_h$, in said hybrid subtraction image by a gain factor, G, which will result in the same relative contrast in said modified hybrid image as in the temporal image and also adding to each hybrid pixel value so multiplied an offset signal value (O*) which will maintain the same relative brightness of the pixels in the H* image as in said temporal image, and replacing the pixel signal values in the region, $R_h$, in said temporal image in said first memory with corresponding modified hybrid image pixel signal values to provide for display of said modified hybrid image in said region $R_h$ in the temporal image.

7. A digital subtraction angiography method for replacing regions in a temporal subtraction image that contain motion artifacts with a modified hybrid subtraction image to enable visualization of an X-ray contrast medium filled blood vessel that is obscured by an artifact, comprising:

expose a portion of the anatomy containing a blood vessel of interest to alternate low and high kV X-ray beams before (pre-contrast) and after (post-contrast) an X-ray contrast medium has reached the vessel, subtract the resulting pre-contrast and post-contrast low kV images and the high kV pre-contrast and post-contrast images or integrations of equal numbers of low kV and high kV pre-contrast and post-contrast images to yield a low kV temporal subtraction image ($I_l$) and a high kV temporal subtraction image ($I_h$), respectively, and store the digital values representing the intensities of the picture elements (pixels) composing these images, store the digital pixel values for preferably $I_l$ in a display controller memory in locations corresponding to the pixel locations in the images and convert the pixel values to analog video signals for driving a video monitor to display the low kV temporal image $I_l$, define in said displayed temporal subtraction image in any order a region, $R_a$, whose pixel intensities are representative of an artifact; a region, $R_s$, whose pixel intensities are representative of an X-ray contrast medium in a blood vessel; a region, $R_b$, whose pixel intensities are representative of background or offset in the image signal values; and, a region, $R_h$, containing artifact which region is to be replaced with a modified hybrid image, within the background region, $R_b$, form the sums of all pixel intensity values separately in the low and high kV temporal subtraction images to produce the offset values $LO_l$ and $LO_h$, respectively, where L indicates the number of pixels in region, $R_b$, within the artifact region, $R_a$, form the sums $A_l$ and $A_h$ of all the pixel intensity values in the low and high kV temporal subtraction images, respectively, where $$A_l = \sum_{j=1}^{N} I_{a,l,j} - NO_l$$

$$A_h = \sum_{j=1}^{N} I_{a,h,j} - NO_h$$

and N is the number of pixels in the defined artifact region, $R_a$, compute the optimal weighting coefficient, k, that will cancel the artifact in a new hybrid subtraction image H* where $$k = \frac{A_l}{A_h},$$

produce, a hybrid subtraction image (H) expressed as $H = I_l - kI_h$ where the coefficient "k" has a value by which the high kV image digital pixel intensity values must be multiplied for artifacts in the low and high kV temporal subtraction images caused by tissue motion between pre-contrast and post-contrast images to cancel when the images are subtracted such that the signal values due to the contrast medium will remain, within the contrast medium region, $R_s$, form the sums $S_l$ and $S_h$ of all the pixel intensity values in the low and high kV temporal subtraction images, respectively, where $$S_l = \sum_{j=1}^{M} I_{s,l,j} - MO_l$$

$$S_h = \sum_{j=1}^{M} I_{s,l,j} - MO_h$$

where M is the number of pixels in the contrast medium region, $R_s$, define a new hybrid image, H*, expressed as $$H^* = G(I_l - kI_h) + O^* = G(H) + O^* \qquad \text{(Eq. 6)}$$

where G is a gain factor that maintains the same contrast in the new hybrid image as is present in the temporal subtraction image relative to the intensity of the X-ray contrast medium in the displayed temporal subtraction image, O* is an offset (background above no signal) value that maintains the background at the same intensity as in the low kV temporal subtraction image, and $(I_l - kI_h)$ is equivalent to H, the first unmodified hybrid image and, $$G = \left(1 - \frac{A_l}{A_h} \cdot \frac{S_h}{S_l}\right)^{-1} \text{ and,}$$

$$O^* = O_l \left[1 - G\left(1 - k\frac{O_h}{O_l}\right)\right]$$

calculate H* by multiplying all pixel values in the region, $R_h$, in the hybrid subtraction image, H, by G and add the value of O* to each pixel to produce the pixel values for the new hybrid image H* within the same region $R_h$ that was defined in the displayed temporal subtraction image, replace the pixel values in said display controller memory representing the temporal subtraction image, only in the region $R_h$, with the just previously calculated pixel values, H*, to substitute the new hybrid subtraction image in the temporal subtraction image for display of the single image on the video monitor.

8. Digital subtraction angiography apparatus adapted for substituting a modified hybrid subtraction image in a defined region of a temporal subtraction image, comprising:

means for producing digital pixel signal arrays representative of a temporal subtraction X-ray image and a hybrid subtraction X-ray image, respectively, a video display controller having a memory for storing the digital temporal subtraction image signal values and means for converting said digital signal values to analog video signals for controlling a television monitor to display said image, a digital video processor operative to modify the digital pixel signal values representative of the hybrid subtraction image by multiplying each of the hybrid image pixel values by a gain factor and adding to each an offset value, and to store the resulting modified hybrid image signal array in a digital memory, to provide for selecting digital pixel signals in a defined region in said modified signal array for substitution in a corresponding region in said temporal subtraction image, another memory means having input and output means, a memory array and an input register in which input digital data is stored until said memory means is enabled to write said data in the array, means coupling said another memory input means to said memory storing the hybrid digital pixel signals and means coupling said output means to said display controller memory, a system controller having data representative of the locations of the pixels in the hybrid image that are to be written into said corresponding location in said display controller memory to patch at least a part of said modified hybrid image into said temporal subtraction image, write address control means and read address control means for said another memory, said write address control means responding to enabling signals by enabling pixel data to be addressed from said input register to said another memory array and said read address control responding to the same enabling signals by enabling said read address control means to read out the data in the addressed locations simultaneously, said system controller providing said enabling signals only when the locations of said pixels in said defined region in said hybrid image are reached as said pixels are being coupled to the input means of said other memory such that only those hybrid image pixel values in said defined region are addressed to locations in said another memory, and only those hybrid image pixel values are coupled to said display controller memory to replace pixels at corresponding locations in said temporal image.

* * * * *